United States Patent [19]
Sato et al.

[11] Patent Number: 5,567,416
[45] Date of Patent: Oct. 22, 1996

[54] SLOW-VOLATILIZING TERPENOID COMPOSITION

[75] Inventors: Shoichi Sato, Machida; Toshi Tabuchi, Yamato; Shigeo Urushida, Kodaira; Sakae Shimizu, Chigasaki, all of Japan

[73] Assignee: Ricoh Company, Ltd., Tokyo, Japan

[21] Appl. No.: 158,399

[22] Filed: Nov. 29, 1993

[30] Foreign Application Priority Data

Nov. 30, 1992 [JP] Japan ................................. 4-345425

[51] Int. Cl.$^6$ ....................................... A61L 9/04
[52] U.S. Cl. .......................................... 424/76.4; 424/486
[58] Field of Search .................................. 424/486, 487, 424/76.21, 76.3, 76.4, 76.8, 76.9, 409; 514/774; 530/354, 355, 402, 410; 523/102, 122; 525/54.1, 903

[56] References Cited

U.S. PATENT DOCUMENTS

| | | | |
|---|---|---|---|
| 4,164,561 | 8/1979 | Hautmann | 424/76.4 |
| 4,294,921 | 10/1981 | Yamaguchi et al. | 525/54.1 |
| 4,301,043 | 11/1981 | Sato et al. | 424/76.4 |
| 4,343,854 | 8/1982 | Moorman | 524/466 |
| 4,898,727 | 2/1990 | Osada et al. | 424/76.3 |
| 4,906,488 | 3/1990 | Pera | 424/76.3 |

*Primary Examiner*—Edward J. Webman
*Attorney, Agent, or Firm*—Oblon, Spivak, McClelland, Maier & Neustadt, P.C.

[57] ABSTRACT

A slow-volatilizing composition is composed of at least one terpenoid, an antioxidant, and an oil-absorbing polymeric network material on which the terpenoid and the antioxidant are absorbed. A non-combustible organic material may be optionally adsorbed on the oil-absorbing polymeric network material.

10 Claims, No Drawings

SLOW-VOLATILIZING TERPENOID COMPOSITION

BACKGROUND OF THE INVENTION

1. Field of the Invention

The present invention relates to a slow-volatilizing composition, and more particularly to a volatilizing composition from which as an effective component terpenoid, which spreads fragrance and has disinfectant, insecticidal, and deodorant or ozone-decomposing properties, is slowly volatilized.

2. Discussion of Background

In order to cause an aromatic agent to be evaporated slowly for an extended period of time, in the case of a liquid aromatic agent, the liquid aromatic agent is adsorbed on the surfaces of finely-divided particles, and the aromatic-agent-adsorbed particles are fixed to a binder agent, thereby preparing an aromatic composition in a predetermined shape from which an effective component of the aromatic agent gradually evaporates. Alternatively, a liquid aromatic agent is placed in a sealed container, and an opening is formed in the container from which an effective agent of the liquid aromatic agent is caused to gradually evaporate.

The above-mentioned conventional methods, however, have the shortcomings that the average amount of the effective component of the aromatic composition evaporated per unit time is not always constant, and the evaporation does not last for an extended period of time. More specifically, a large amount of an aromatic agent is apt to initially evaporate, and the amount of evaporation rapidly decreases with time.

Furthermore, it is difficult to maintain the predetermined shape of the above-mentioned aromatic composition comprising an aromatic agent which is contained in a binder agent until the contained aromatic agent is completely evaporated, and therefore it is not always convenient to use.

SUMMARY OF THE INVENTION

It is therefore an object of the present invention to provide a slow-volatilizing composition free from the above-mentioned shortcomings of the conventional aromatic compositions, from which an effective component is constantly evaporated for an extended period of time, thereby maintaining its effect for an extended period of time, with the shape of the composition being substantially maintained the same until the effect component is completely evaporated therefrom.

This object of the present invention can be achieved by a slow-volatilizing composition comprising at least one terpenoid, an antioxidant, and an oil-absorbing polymeric network material on which the terpenoid and the antioxidant are absorbed.

According to the present invention, a non-combustible organic material may further be adsorbed on the oil-absorbing polymeric network material.

DETAILED DESCRIPTION OF THE PREFERRED EMBODIMENTS

The slow-volatilizing composition according to the present invention comprises at least one terpenoid, an antioxidant, and an oil-absorbing polymeric network material on which the terpenoid and the antioxidant are absorbed.

As mentioned above, in the slow-volatilizing composition according to the present invention, an antioxidant is used in combination with terpenoid. This is because terpenoid, in particular, a monocyclic terpenoid, is easily oxidized, so that when the terpenoid is oxidized, it becomes an alcohol, and the thus formed alcohol flows slowly from the oil-absorbing polymeric network material. The anti-oxidant is used in order to prevent the above-mentioned oxidation of the terpenoid.

Furthermore, according to the present invention, if necessary, a non-combustible organic material may further be adsorbed on the oil-absorbing polymeric network material. This is because the terpenoid is generally flammable, and the non-combustible organic material is added to minimize the risk of the terpenoid catching fire.

Terpenoids have been used as raw materials for aromatics and medicines from ancient times. Camphor is an important material for use in the chemical industry and recently has been used as an ozone-removing agent as disclosed in Japanese Patent Publication 2-30729.

Hydrocarbons such as monoterpenes and sesquiterpenes, and alcohol-, aldehyde- and ketone-derivatives of terpenes can be employed as the terpenoids for use in the present invention. Specific examples of such terpenoids are santene, cryptone, cyclogeraniolene, myrcene, ocimene, limonene, carene, pinene, bornylene, orthodene, geraniol, linalool, terpineol, borneol, citronellal, citral, nopol, ionone, parmone, irone, sesquibenihiol, farnesol, atlantone, and turmerone.

Of these terpenoids, monocyclic and chain terpenoids represented by $C_{10}H_{16}$, such as d-limonene, are most effective.

The above-mentioned terpenoids can be used individually or in combination.

d-limonene is a colorless or light yellow transparent liquid, with a flash point of 45° C. and a boiling point of 176° C., which can be obtained in the form of an essential oil from the skins of oranges. It has a fragrance characteristic of citrus fruits, and is used as an aromatic oil and as a component for aromatics.

When d-limonene is used, a fragrant slow-volatilizing composition which is not deformed while in use can be obtained.

Furthermore, d-limonene is better than other terpenoids in terms of the properties of decomposing ozone through a redox reaction therewith since it easily reacts with ozone, and also in terms of the properties of decomposing $NO_x$.

Therefore the slow-volatilizing composition comprising d-limonene is effective for decomposing ozone if it is disposed at a place where ozone is generated, for instance, in or around electric appliances using high voltage, such as plain paper copiers and laser printers, and in water-processing apparatus for cleaning water, and air-cleaning apparatus for cleaning air by using ozone, from which ozone is emitted.

As an antioxidant for use in the present invention, it is preferable to use a phenol compound having a bulky group, that is, a compound having a hindered phenol structural unit, namely a compound comprising within its molecule at least a structural unit of the following formula (I) or a structural unit of the following formula (II), which is a phenol compound with a bulky group,

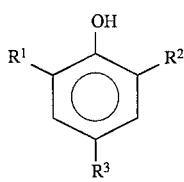

(I)

wherein $R^1$, $R^2$, and $R^3$ independently represent a straight or branched alkyl group having 1 to 4 carbon atoms, such as methyl group, ethyl group, propyl group, i-propyl group, butyl group, sec-butyl group, and t-butyl group.

Of these alkyl groups, t-butyl group is most preferable.

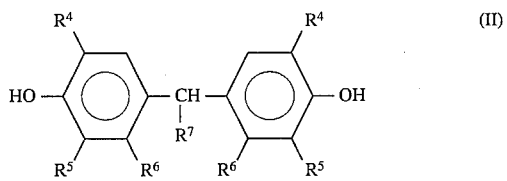

(II)

wherein $R^4$, $R^5$ and $R^6$ each represent a straight or branched alkyl group with 1 to 18 carbon atoms, such as methyl group, ethyl group, pentyl group, octyl group, and dodecyl group, and $R^7$ represents hydrogen, or an alkyl group with 1 to 10 carbon atoms, such as methyl group, ethyl group, butyl group, t-butyl group, hexyl group, and nonyl group.

As other anti-oxidants for use in the present invention, butylhydroxy anisole having in its molecule a phenyl group, dl-α-tocopherol, and 4,4'-thiobis(3-methyl-6-t-butylphenol) are preferably employed.

The slow-volatilizing composition of the present invention comprises at least one of the above-mentioned terpenoids, and one of the above-mentioned antioxidants, which are adsorbed on an oil-absorbing polymeric network material.

The oil-absorbing polymeric network material is composed of a self-swelling oil-absorbing resin, which is a polymer with a low degree of cross-linking prepared basically from a lipophilic monomer and is capable of incorporating a large amount of oils into the molecule thereof. The incorporation of oils into the polymer is considered to be carried out based on the driving force generated by the mutual interaction of the lipophilic groups within the polymer and the molecules of oils. Oil-absorbing polymeric network materials containing 0.001–2 wt. % cross-linking agents are disclosed, for instance, in Japanese Laid-Open Patent Applications 50-15882, 50-59486, and 50-94092.

Such an oil-absorbing polymeric network material is capable of absorbing terpenoids in an amount equivalent to 10 times the weight of the oil-absorbing polymeric network material, so that the life of the slow-volatilizing composition of the present invention per unit weight thereof is about 1.5 times the life of volatile compositions using conventional carriers for terpenoids.

Furthermore, as mentioned previously, it is also preferable that a non-combustible organic material be adsorbed on the oil-absorbing polymeric network material, together with the terpenoide and antioxidant.

The slow-volatilizing composition of the present invention can be made non-combustible or flame retardant by incorporating a halogen-based flame retarder or a phosphorous-based flame retarder into the oil-absorbing polymeric network material by mixing or dispersing such a flame retarder in the oil-absorbing polymeric network material. These methods, however, tend to be complicated and difficult.

Under such circumstances, the inventors of the present invention have tested a method of causing the oil-absorbing resin to absorb a mixture of a halogenated hydrocarbon (non-combustible organic liquid compound) and terpenoide in view of the fact that the oil-absorbing resin is capable of absorbing chloroform, carbon tetrachloride, trichloroethane, and trichloroethylene in an amount of about 20 times the weight of the oil-absorbing resin. As a result, it has been confirmed that methylene chloride, trichloroethylene, perchloroethylene, 1,1,1-trichloroethane, 2,3-dibromo-1-propanol, pentafluoropropanol, HCFC225ca (1,1-dichloro-2,2,3,3,3-pentafluoro propane), and HCF225cd (1,3-dichloro-1,2,2,3,3-pentafluoropropane), when mixed with terpenoid, particularly when mixed with d-limonene, can provide a composition which has no risk of catching fire when used in practice. Preferable non-combustible organic compounds for use in the above are methylene chloride, pentafluoropropanol, and HCFC225, and when the destructive effect of such non-combustible organic compounds on the ozone layer is taken into consideration, HCFC225 is preferable for use in the present invention.

The slow-volatilizing composition of the present invention is prepared by the steps of (1) preparing a mixed liquid composed of a terpenoid (preferably a monocyclic terpene, more preferably d-limonene) and an antioxidant, (2) adding a non-combustible organic compound to the above prepared mixed liquid, (3) immersing an absorbing polymeric network material in the above prepared mixed liquid, causing the mixed liquid to be sufficiently absorbed on the oil-absorbing polymeric network material, and (4) drying the mixed-liquid-absorbed polymeric network material at room temperature.

There is no particular limitation on the amount of each of the terpenoid, the antioxidant, and the non-combustible organic compound which are absorbed by the oil-absorbing polymeric network material as long as they are appropriately absorbed by the polymeric network material. However, generally it is preferable that the amount of the antioxidant be in the range of 5 to 30 parts by weight to 100 parts by weight of the terpenoid, and the amount of the non-combustible organic compound be in the range of 10 to 100 parts by weight to 100 parts by weight of the terpenoid.

Other features of this invention will become apparent in the course of the following description of exemplary embodiments, which are given for illustration of the invention and are not intended to be limiting thereof.

EXAMPLE 1

A sheet-shaped, transparent, solid oil-absorbing resin, which is hereinafter referred to as the oil-absorbing resin, was prepared as follows:

0.5 g of gelatin was dissolved in 170 ml of deionized water to prepare an aqueous solution of gelatin. To this aqueous solution of gelatin, 50 g of tert-butyl methacrylate, 0.025 g of divinylbenzene and 0.25 g of benzoyl peroxide were added. Nitrogen was blown through the above mixture to remove oxygen therefrom.

The thus prepared reaction mixture was heated to 80° C. with stirring, and vigorously stirred at the same temperature for 7 hours for polymerization, whereby a polymer was produced.

The thus produced polymer was separated from the reaction mixture by filtration, washed and dried, so that 48 g of polymer particles with an average particle size of 0.95 mm was obtained. The thus obtained polymer particles were formed into a polymer sheet. The polymer sheet was cut into a rectangular parellepiped of 2 cm×4 cm×1 cm, whereby a highly oil-absorbing resin sample was prepared. The thus prepared oil-absorbing resin sample weighed 4.40 g.

This oil-absorbing resin sample was immersed in a mixed liquid composed of d-limonene (70 wt. %) and HCFC225 (30 wt. %) for 210 hours. After this immersion, the oil-absorbing resin sample was dried at room temperature, whereby an oil-absorbing resin sample No. 1 was obtained. The thus obtained dried oil-absorbing resin sample No. 1 weighed 49.00 g, and the size thereof was expanded to 4.5 cm×8.5 cm×2.5 cm.

EXAMPLE 2

Polymer particles were prepared in accordance with the same polymerization procedure as in Example 1, and the prepared polymer particles were formed into a polymer sheet. The polymer sheet was cut into a rectangular parellepiped of 2 cm×4 cm×1 cm as in Example 1.

This oil-absorbing resin sample was immersed in a mixed liquid composed of d-limonene (90 wt. %) and methylene chloride (10 wt. %) for 210 hours. After this immersion, the oil-absorbing resin sample was dried at room temperature, whereby an oil-absorbing resin sample No. 2 was obtained.

Comparative Example 1

Polymer particles were prepared in accordance with the same polymerization procedure as in Example 1, and the prepared polymer particles were formed into a polymer sheet. The polymer sheet was cut into a rectangular parellepiped of 2 cm×4 cm×1 cm as in Example 1, whereby a highly oil-absorbing resin sample was obtained. The thus-prepared oil-absorbing resin sample weighed 4.26 g.

This oil-absorbing resin sample was immersed in d-limonene (100%). It was confirmed that even if the immersion was continued for more than 210 hours, d-limonene was not further absorbed by the oil-absorbing resin sample. Thus, the time period of 210 hours was determined as the absorption saturation time.

After this immersion, the oil-absorbing resin sample was dried at room temperature, whereby a comparative oil-absorbing resin sample No. 1 was obtained. The weight of the thus prepared dried oil-absorbing resin sample was found to have increased to 47.64 g, and the size thereof was expanded to 5 cm×9 cm×2.5 cm.

Each of the above oil-absorbing resin samples No. 1 and No. 2, which were respectively prepared in Example 1 and Example 2, and the comparative oil-absorbing resin sample No. 1 prepared in Comparative Example 1 was subjected to a flammability investigating test in a constant-temperature chamber.

The oil-absorbing resin sample No. 1 exhibited a flash point of 68.0° C. because of the non-flammable effect of HCFC-225 and it was confirmed that this material does not have any risk of being flammable in practical use at room temperature.

The oil-absorbing resin sample No. 2 exhibited a flash point of 70° C., indicating excellent non-flammability.

The comparative oil-absorbing resin sample No. 1 exhibited a flash point of 45.5° C., which is close to the flash point of d-limonene.

Each of the oil-absorbing resin samples No. 1 and No. 2 and the comparative oil-absorbing resin sample No. 1 was allowed to stand at 40° C. in a constant-temperature chamber for 30 days. As a result, it was found that a large amount of the absorbed liquid flowed from each of the resin samples.

It is considered that this was because the double bond moiety of d-limonene employed was oxidized so that the d-limonene was partly converted to an alcohol and the intermolecular force between the oil-absorbing polymeric network material and the d-limonene became weak, and the d-limonene which was partly converted to an alcohol flowed from each oil-absorbing resin sample.

EXAMPLE 3

A mixed liquid composed of 59.2 g of d-limonene and 45.8 g of HCFC-225 was prepared.

1 g, 3 g, 5 g, and 8 g of dibutylhydroxy toluene serving as an antioxidant for d-limonene were respectively added to the above prepared mixed liquid, whereby 4 kinds of solutions were obtained.

In the same manner, 1 g, 3 g, 5 g, and 8 g of dl-α-tocopherol serving as an antioxidant for d-limonene were respectively added to the above prepared mixed liquid, whereby 4 kinds of solutions were obtained.

Thus, 8 kinds of solutions were obtained.

Eight oil-absorbing resin samples, each of 2 cm×4 cm×1 cm, which were exactly the same as the oil-absorbing resin sample prepared in Comparative Example 1 were prepared.

These eight oil-absorbing resin samples were respectively immersed in the above prepared eight kinds of solutions and were allowed to stand for 210 hours. These oil-absorbing resin samples which swelled from the immersion were taken out and dried at room temperature.

These 8 kinds of the dried oil-absorbing resin samples No. 1 to No. 8 were allowed to stand at 50° C., 60% RH in a constant-temperature chamber for 30 days to see if d-limonene oozed from each of these oil-absorbing resin samples during a period of 30 days.

Results are shown in the following Table 1:

TABLE 1

| Sample No. | Dibutylhydroxy toluene/ mixed liquid composed of d-limonene and HCFC-225 | Time period before of d-limonene oozed |
|---|---|---|
| 1 | 1 g / 105 g | 5 days |
| 2 | 3 g / 105 g | 15 days |
| 3 | 5 g / 105 g | *30 days |
| 4 | 8 g / 105 g | *30 days |

| Sample No. | dl-α-tocopherol/ mixed liquid composed of d-limonene and HCFC-225 | Time period before d-limonene oozed |
|---|---|---|
| 5 | 1 g / 105 g | 5 days |
| 6 | 3 g / 105 g | 12 days |
| 7 | 5 g / 105 g | *30 days |
| 8 | 8 g / 105 g | *30 days |

The results shown in Table 1 indicate that both antioxidants, that is, dibutylhydroxy toluene and dl-α-tocopherol, had sufficient antioxidation effect for use in the present invention, and that when the amount of the antioxidant was 5 g or more (Samples No. 3, No. 4, No. 7 and No. 8), d-limonene did not ooze at 50° C. even after 30 days, which is indicated by "*30 days" in the above Table 1. In other words, d-limonene was not converted to an alcohol by the antioxidation effect of these antioxidants even after 30 days.

EXAMPLE 4

The same procedure as in Example 3 was repeated except that the d-limonene employed in each of the eight kinds of solutions employed in Example 3 was replaced by a mixed liquid composed of 70 wt. % of d-limonene and 30 wt. % of β-myrcene, whereby 8 kinds of solutions were obtained.

Eight oil-absorbing resin samples, each of 2 cm×4 cm×1 cm, which were exactly the same as the oil-absorbing resin sample prepared in Comparative Example 1 were prepared.

These eight oil-absorbing resin samples were respectively immersed in the above prepared eight kinds of solutions and were allowed to stand for 210 hours. These oil-absorbing resin samples which swelled from the immersion were taken out and dried at room temperature.

These 8 kinds of the dried oil-absorbing resin samples No. 9 to No. 16 were allowed to stand at 50° C., 60% RH in a constant-temperature chamber for 30 days to see if d-limonene oozed from these oil-absorbing resin samples during a period of 30 days.

Results are shown in the following Table 2:

TABLE 2

| Sample No. | Dibutylhydroxy toluene/ mixed liquid composed of a mixture of d-limonene (70 wt. %) and β-myrcene (30 wt. %), and HCFC-225 | Time period before d-limonene oozed |
| --- | --- | --- |
| 9 | 1 g / 105 g | 5 days |
| 10 | 3 g / 105 g | 15 days |
| 11 | 5 g / 105 g | *30 days |
| 12 | 8 g / 105 g | *30 days |

| Sample No. | dl-α-tocopherol/ mixed liquid composed of a mixture of d-limonene (70 wt. %) and β-myrcene (30 wt. %), and HCFC-225 | Time period before d-limonene oozed |
| --- | --- | --- |
| 13 | 1 g / 105 g | 5 days |
| 14 | 3 g / 105 g | 12 days |
| 15 | 5 g / 105 g | *30 days |
| 16 | 8 g / 105 g | *30 days |

The results shown in Table 2 indicate that both antioxidants, that is, dibutylhydroxy toluene and dl-α-tocopherol, had sufficient antioxidation effect for use in the present invention, and that when the amount of the antioxidant was 5 g or more (Samples No. 11, No. 12, No. 15, and No. 16), d-limonene did not ooze at 50° C. even after 30 days.

EXAMPLE 5

The same procedure as in Example 3 was repeated except that the d-limonene employed in each of the eight kinds of solutions employed in Example 3 was replaced by a mixed liquid composed of 50 wt. % of d-limonene and 50 wt. % of linalool, whereby 8 kinds of solutions were obtained.

Eight oil-absorbing resin samples, each of 2 cm×4 cm×1 cm, which were exactly the same as the oil-absorbing resin sample prepared in Comparative Example 1 were prepared.

These eight oil-absorbing resin samples were respectively immersed in the above prepared eight kinds of solutions and allowed to stand for 210 hours. These oil-absorbing resin samples which swelled from the immersion were taken out and dried at room temperature.

These 8 kinds of the dried oil-absorbing resin samples No. 17 to No. 24 were allowed to stand at 50° C., 60% RH in a constant-temperature chamber for 30 days to see if d-limonene oozed from these oil-absorbing resin samples during a period of 30 days.

Results are shown in the following Table 3:

TABLE 3

| Sample No. | Dibutylhydroxy toluene/ mixed liquid composed of an aromatic composed of d-limonene (50 wt. %) and linalool (50 wt. %), and HCFC-225 | Time period before d-limonene oozed |
| --- | --- | --- |
| 17 | 1 g / 105 g | 5 days |
| 18 | 3 g / 105 g | 15 days |
| 19 | 5 g / 105 g | *30 days |
| 20 | 8 g / 105 g | *30 days |

| Sample No. | dl-α-tocopherol/ mixed liquid composed of an aromatic composed of d-limonene (50 wt. %) and linalool (50 wt. %), and HCFC-225 | Time period before d-limonene oozed |
| --- | --- | --- |
| 21 | 1 g / 105 g | 5 days |
| 22 | 3 g / 105 g | 12 days |
| 23 | 5 g / 105 g | *30 days |
| 24 | 8 g / 105 g | *30 days |

The results shown in Table 3 indicate that both antioxidants, that is, dibutylhydroxy toluene and dl-α-tocopherol, had sufficient antioxidation effect for use in the present invention, and that when the amount of the antioxidant was 5 g or more (Samples No. 19, No. 20, No. 23 and No. 24), d-limonene did not ooze at 50° C. even after 30 days.

EXAMPLE 6

1.0 g of gelatin was dissolved in 170 ml of deionized water to prepare an aqueous solution of gelatin. To this aqueous solution of gelatin, 50 g of para tert-butyl styrene, 0.05 g of ethylene dimethacrylate and 0.1 g of azobisisobutyronitrile were added. Nitrogen was blown through the above reaction mixture at room temperature, whereby oxygen was removed from the reaction mixture.

The thus prepared reaction mixture was heated to 60° C. with stirring for 6 hours. At this moment, the polymerization reaction ratio reached about 60%. With the temperature of the reaction mixture elevated to 80° C., the polymerization reaction was further continued while stirring the reaction mixture for 2 hours, whereby a polymer was produced.

The thus produced polymer was separated from the reaction mixture by filtration, washed and dried, so that 47 g of polymer particles with an average particle size of 0.6 mm was obtained. The thus obtained polymer particles were formed into a polymer sheet with a weight of 10 g. The polymer sheet was placed in a vessel and a solution composed of 70 g of d-limonene, 30 g of HCFC225, and 5 g of dibutylhydroxy toluene was poured onto the above polymer sheet. The polymer sheet was allowed to stand in such a state for 210 hours. The polymer sheet became like a transparent agar-like sheet and the poured solution was completely absorbed by the polymer sheet.

The thus prepared sample was allowed to stand at 50° C., 60% RH in a constant-temperature chamber for 30 days to see if the absorbed d-limonene was converted to an alcohol and flowed out. The result was that the d-limonene was not converted to an alcohol and did not flow out.

EXAMPLE 7

The d-limonene evaporation rate of each of Samples No. 3 and No. 7, which were prepared in Example 3, was measured under the following conditions:

Sample No. 3 was placed in a cylindrical container with a diameter of 55 mm and a depth of 75 mm, having an opening of 55 mm which was fully opened, and was allowed to stand at room temperature for one day, in a calm state without any particular air flow in the atmosphere. The amount of the evaporated d-limonene was 1.16 g per day.

The above test was repeated in the same manner except that the opening was narrowed to 2 mm by partially sealing the opening with an aluminum sheet. The result was that the amount of the evaporated d-limonene was 10 mg per hour.

The same tests as in the above were conducted with respect to Sample No. 7. Results are shown in the following Table 4.

Sample No. 3 and Sample No. 7 were further subjected to an ozone removal performance test and a $NO_x$ removal performance test to investigate the ozone removal performance and $NO_x$ removal performance thereof, respectively.

In the ozone removal performance test, Sample No. 3 placed in the above-mentioned cylindrical container with the diameter of the opening thereof set at 2 mm, was placed in a large desiccator, and an ozone-containing air with a 3 ppm ozone concentration was introduced into the desiccator through a tube. A mixed gas of the ozone, air and d-limonene which was evaporated from Sample No. 3 and was allowed to react with the ozone, was sucked from the desiccator through a tube, and the concentration of ozone in the mixed gas was measured by an ozone monitor.

The result was that the ozone with a concentration of 3 ppm was decomposed to a concentration of about 0.15 ppm per hour, which was equivalent to a 95% ozone decomposition rate per hour.

The same ozone removal test as mentioned above was conducted with respect to Sample No. 7. Results are shown in Table 4. The ozone decomposition rate of Sample No. 7 was 96% per hour.

In the above measurement, the flow rates of the ozone-containing air and the mixed gas through the desiccator and the tubes, the pressures thereof and the suction rate were appropriately controlled. This method is referred to as the desiccator measurement method.

The $NO_x$ removal performance test was also conducted by the above desiccator measurement method, in which Sample No. 3 placed in the above-mentioned cylindrical container with the opening thereof fully opened (55 mm in diameter), was placed in a large desiccator, and a $NO_x$-containing air with a concentration of 0.53 ppm was introduced into the desiccator through a tube. A mixed gas of the $NO_x$, air and d-limonene which was evaporated from Sample No. 3 and allowed to react with the ozone, was sucked from the desiccator through a tube, and the concentration of $NO_x$ in the mixed gas was measured. The result was that the average $NO_x$ decomposition rate was as low as 26% per hour, although the container for Sample No. 3 was fully opened. However it was found that the $NO_x$ decomposition ratio was increased as the reaction time was lengthened.

The same $NO_x$ removal test as mentioned above was conducted with respect to Sample No. 7. Results are shown in Table 4. The average $NO_x$ decomposition rate of Sample No. 7 was 27% per hour.

TABLE 4

| Sample | Amount of d-limonene Evaporated | Ozone-Removal Ratio | $NO_x$- Removal Ratio |
|---|---|---|---|
| No. 3 | 1.16 g/day/ fully opened 10 mg/hr/ 2 mm φ | (Initial Value: $O_3$ = 3 ppm) Average 95%/ 2 mm φ /hr | (Initial Value: $NO_x$ = 0.53 ppm) Average 26%/ 55 mm φ /hr |
| No. 7 | 1.14 g/day/ fully opened 10 mg/ hr/2 mm φ | (Initial Value: $O_3$ = 3 ppm) Average 96%/ 2 mm φ /hr | (Initial Value: $NO_x$ = 0.53 ppm) Average 27%/ 55 mm φ /hr |

The slow-volatilizing composition according to the present invention comprises an oil-absorbing polymeric network material, a large amount of terpenoid which is absorbed on the oil-absorbing polymeric network material, and an antioxidant for preventing the oxidation of the terpenoid, which makes it possible to prevent the oxidation of the terpenoid and to lengthen the evaporation period of the terpenoid serving as an effective component of the slow-volatilizing composition in such a manner as to make the evaporation constant throughout the period.

Furthermore, by causing a non-combustible organic material to be adsorbed on the oil-absorbing polymeric network material of the composition, the flash point of the composition is substantially increased, whereby the safety of the composition while in use is significantly increased.

What is claimed is:

1. A slow-volatilizing composition comprising at least one terpenoid, an antioxidant, an oil-absorbing polymeric network containing 0.001–2 wt. % cross-linking monomers on which said terpenoid and said antioxidant are absorbed, wherein said polymeric network absorbs said terpenoid in an amount equal to 10 times the weight of said polymeric network and wherein said polymeric network absorbs chloroform, carbon tetrachloride, trichloroethane and trichloroethylene in an amount of 20 times the weight of said polymeric network, and a non-combustible organic compound which is adsorbed on said oil-absorbing polymeric network, wherein said composition contains 5–30 parts by weight of said antioxidant to 100 parts by weight of said terpenoid and said composition contains 10–100 parts by weight of said non-combustible organic compound to 100 parts by weight of said terpenoid.

2. The slow-volatilizing composition as claimed in claim 1, wherein said terpenoid is selected from the group consisting of santene, cryptone, cyclogeraniolene, myrcene, ocimene, limonene, carene, pinene, bornylene, orthodene, geraniol, linalool, terpineol, borneol, citronellal, citral, nopol, ionone, parmone, irone, sesquibenihiol, farnesol, atlantone, and turmerone.

3. The slow-volatilizing composition of claim 2, wherein said terpenoid is limonene.

4. The slow-volatilizing composition as claimed in claim 1, wherein said antioxidant is a compound of formula (I)

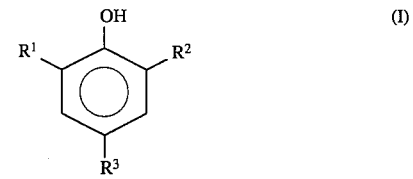

wherein $R^1$, $R^2$, and $R^3$ independently represent a straight or branched alkyl group having 1 to 4 carbon atoms.

5. The slow-volatilizing composition as claimed in claim 4, wherein $R^1$, $R^2$, and $R^3$ independently represent an alkyl group selected from the group consisting of methyl group, ethyl group, propyl group, i-propyl group, butyl group, sec-butyl group, and t-butyl group.

6. The slow-volatilizing composition as claimed in claim 1, wherein said antioxidant is a compound of formula (II)

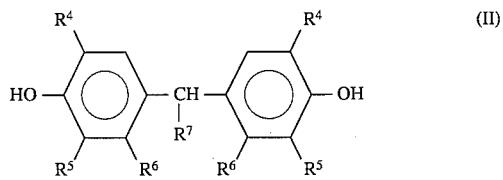

wherein $R^4$, $R^5$ and $R^6$ each represent a straight or branched alkyl group with 1 to 18 carbon atoms, and $R^7$ represents hydrogen, or an alkyl group with 1 to 10 carbon atoms.

7. The slow-volatilizing composition as claimed in claim 6, wherein $R^4$, $R^5$ and $R^6$ each represent an alkyl group selected from the group consisting of methyl group, ethyl group, pentyl group, octyl group, and dodecyl group, and $R^7$ is hydrogen or an alkyl group selected from the group consisting of methyl group, ethyl group, butyl group, t-butyl group, hexyl group, and nonyl group.

8. The slow-volatilizing composition as claimed in claim 1, wherein said antioxidant is selected from the group consisting of a phenyl group-containing butyl hydroxy anisole, dl-α-tocopherol, and 4,4'-thiobis(3-methyl-6-t-butylphenol).

9. A slow-volatilizing composition comprising at least one terpenoid, an antioxidant, an oil-absorbing polymeric network containing 0.001–2 wt. % cross-linking monomers on which said terpenoid and said antioxidant are absorbed, wherein said polymeric network absorbs said terpenoid in an amount equal to 10 times the weight of said polymeric network and wherein said polymeric network absorbs chloroform carbon tetrachloride, trichloroethane and trichloroethylene in an amount of 20 times the weight of said polymeric network, and a non-combustible organic compound which is adsorbed on said oil-absorbing polymeric network, wherein said composition contains 5–30 parts by weight of said antioxidant to 100 parts by weight of said terpenoid and said composition contains 10–100 parts by weight of said non-combustible organic compound to 100 parts by weight of said terpenoid, wherein said non-combustible organic compound is selected from the group consisting of methylene chloride, trichloroethylene, perchloroethylene, 1,1,1-trichloroethane, 2,3-dibromo-1-propanol, pentafluoropropanol, 1,1-dichloro-2,2,3,3,3-pentafluoropropane, and 1,3-dichloro-1,2,2,3,3-pentafluoropropane.

10. The slow-volatilizing composition of claim 9, wherein said terpenoid is limonene.

* * * * *

UNITED STATES PATENT AND TRADEMARK OFFICE
CERTIFICATE OF CORRECTION

PATENT NO. : 5,567,416
DATED : October 22, 1996
INVENTOR(S) : SHOICHI SATO ET AL.

It is certified that error appears in the above-identified patent and that said Letters Patent is hereby corrected as shown below:

Column 4,　　line 10, "HCF225cd"

should read --HCFC225cd--.

Column 6,　　line 41, "Time period before of d-limonene oozed"

should read --Time period before d-limonene oozed--.

Signed and Sealed this

Twenty-fourth Day of March, 1998

Attest:

BRUCE LEHMAN

Attesting Officer　　　　Commissioner of Patents and Trademarks